(12) United States Patent
Jung

(10) Patent No.: US 10,054,523 B2
(45) Date of Patent: Aug. 21, 2018

(54) EMBEDDING CASSETTE, EMBEDDING MOLD AND EMBEDDING ASSEMBLY FOR BIOPSY

(71) Applicant: Sun Mi Jung, Gyeonggi-do (KR)

(72) Inventor: Sun Mi Jung, Gyeonggi-do (KR)

(73) Assignee: Sun Mi Jung, Gyeonggi-do (KR)

( * ) Notice: Subject to any disclaimer, the term of this patent is extended or adjusted under 35 U.S.C. 154(b) by 338 days.

(21) Appl. No.: 14/759,229

(22) PCT Filed: Nov. 27, 2013

(86) PCT No.: PCT/KR2013/010824
§ 371 (c)(1),
(2) Date: Jul. 5, 2015

(87) PCT Pub. No.: WO2014/109480
PCT Pub. Date: Jul. 17, 2014

(65) Prior Publication Data
US 2015/0355059 A1  Dec. 10, 2015

(30) Foreign Application Priority Data

Jan. 14, 2013 (KR) .................. 10-2013-0003852
Apr. 29, 2013 (KR) .................. 10-2013-0047427
Apr. 29, 2013 (KR) .................. 10-2013-0047433

(51) Int. Cl.
*G01N 1/36* (2006.01)
(52) U.S. Cl.
CPC ......... *G01N 1/36* (2013.01); *G01N 2001/366* (2013.01)
(58) Field of Classification Search
CPC .................................................. G01N 1/36
See application file for complete search history.

(56) References Cited

U.S. PATENT DOCUMENTS

| 5,665,398 A | * | 9/1997 | McCormick ............ B29C 39/10 |
| | | | 118/429 |
| 2008/0254504 A1 | | 10/2008 | Vom et al. |
| 2009/0246825 A1 | | 10/2009 | McCormick |
| 2010/0278627 A1 | | 11/2010 | Williamson, IV et al. |

FOREIGN PATENT DOCUMENTS

| JP | 2004-125631 A | 4/2004 |
| JP | 4058709 B2 | 3/2008 |
| JP | 4330732 B2 | 9/2009 |

OTHER PUBLICATIONS

International Search Report for PCT/KR2013/010824.

* cited by examiner

*Primary Examiner* — Jyoti Nagpaul
(74) *Attorney, Agent, or Firm* — The PL Law Group, PLLC

(57) ABSTRACT

Disclosed is an embedding cassette for biopsy to embed tissue received in an embedding mold provided with a space to receive the tissue when the embedding cassette is combined with the embedding mold, including a body provided with a space communicating with the receipt space of the combined embedding mold so that an injected paraffin solution may coagulate therein during embedding of the tissue and at least one paraffin barrier groove formed at the edge of the lower surface of the body, and, when the embedding cassette is combined with the embedding mold and embedding of the tissue is carried out, the injected paraffin solution flows into the at least one paraffin barrier groove and forms a barrier and, thereby, leakage of the paraffin solution between the embedding cassette and embedding mold is prevented.

20 Claims, 14 Drawing Sheets

FIG. 2
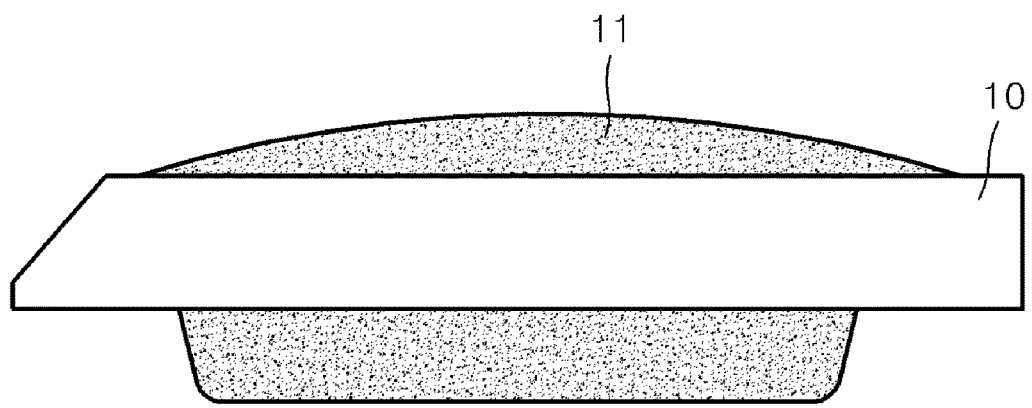
(a)
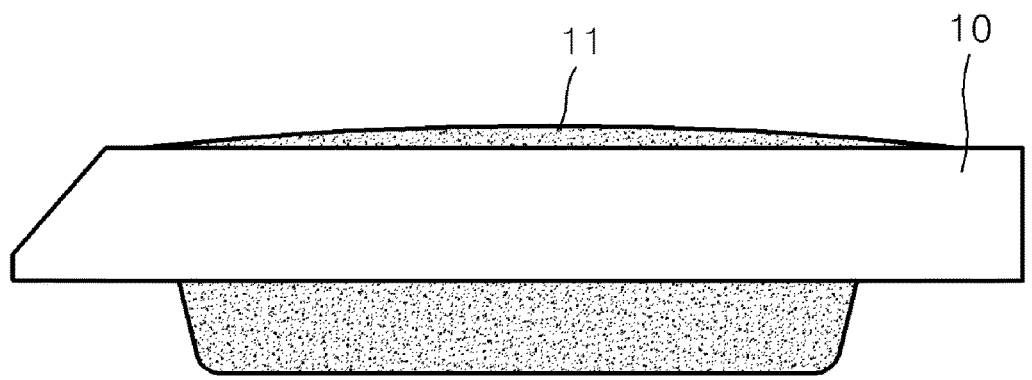
(b)

FIG. 4
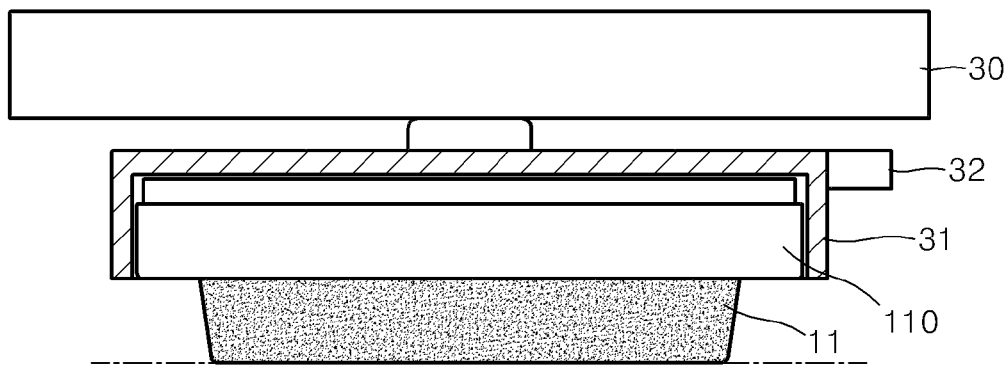
(a)
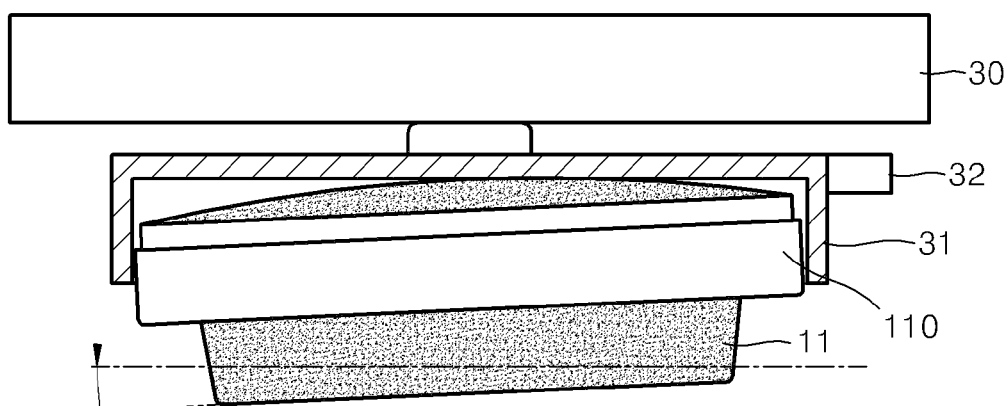
(b)
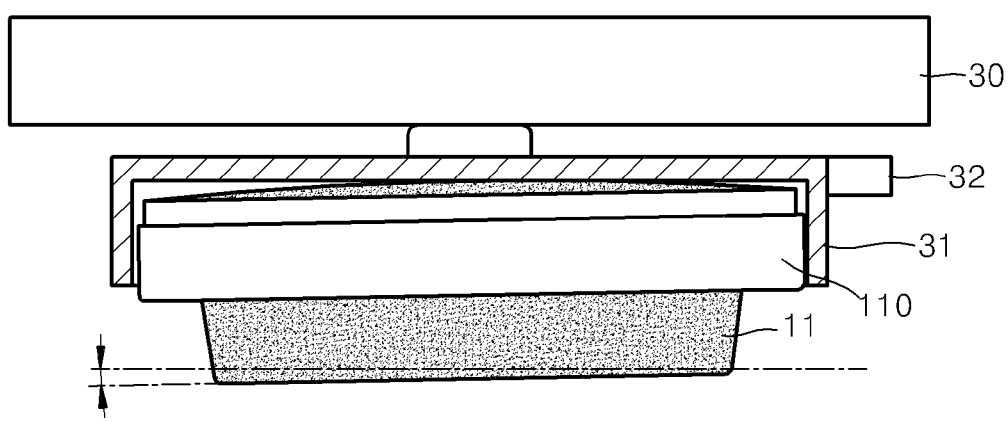
(c)

EMBEDDING CASSETTE, EMBEDDING MOLD AND EMBEDDING ASSEMBLY FOR BIOPSY

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2013/010824, filed 27 Nov. 2013, which claims priority to Korean Patent Application Nos. 10-2013-0003852 filed 14 Jan. 2013, 10-2013-0047427 filed 29 Apr. 2013, and 10-2013-0047433 filed 29 Apr. 2013, the entire contents of which are incorporated herein by reference.

TECHNICAL FIELD

The present invention relates to an embedding mold and an embedding cassette required during a process of manufacturing a paraffin tissue block necessary to execute biopsy, and more particularly to an embedding mold and an embedding cassette required when, in order to execute biopsy, pretreatment of tissue fixed to various fixing agents (dehydration the fixed tissue, transparency of the fixed tissue and permeation of paraffin into the fixed tissue) is performed through 1) a tissue processing process, a paraffin tissue block is made through 2) a paraffin embedding process of the tissue having passed through the tissue processing process, 3) the paraffin tissue block is sliced into a tissue section of a proper thickness using a microtome (a slicing device), and such a section is subjected to immunostaining, general staining, special staining, etc., through a protocols of various staining processes and is then observed with the naked eye using an optical microscope.

That is, the present invention relates to an embedding mold and an embedding cassette required when such a paraffin tissue block is manufactured.

BACKGROUND ART

In general, a biopsy method includes a processing process in which tissue for inspection is put into an embedding cassette and a paraffin solution (formalin) is absorbed into the tissue, an embedding process in which the processed tissue coagulates together with the paraffin solution so as to slice the tissue into a thickness for biopsy, a slicing process in which the embedding cassette provided with the coagulated paraffin solution is fixed to a slicing device so as to slice the coagulated tissue together with the paraffin solution into a section of a predetermined thickness, and an inspection process in which the processed and sliced section s dissolved and inspected.

Here, an embedding assembly for biopsy used in the conventional biopsy method includes an embedding cassette 10 and an embedding mold 20, as exemplarily shown in FIG. 1, and the embedding cassette 10 is placed on or combined with the embedding mold 20 and then used during the embedding process of embedding tissue in paraffin.

Therefore, during the conventional embedding process to manufacture a paraffin tissue block, processed tissue is put into the embedding mold 20, the embedding cassette 10 is seated on the embedding mold 20, and a paraffin solution 11 in a liquid state is supplied to the embedding mold 20 through the embedding cassette 10 so as to fill the embedding mold 20 and then coagulates, thus manufacturing a paraffin tissue block.

However, the embedding process is generally manually carried out and may thus cause several problems.

Among them, one problem occurs during the embedding process in which the paraffin solution is injected into the embedding mold and the embedding cassette so as to embed the tissue.

Since the above-described embedding process is manually carried out and thus a precise amount of the paraffin solution may not be injected into the embedding cassette combined with the embedding mold, the paraffin solution 11 may coagulate under the condition that the paraffin solution 11 overflows the surface of the embedding cassette.

When the paraffin solution 11 coagulates under the condition that the paraffin solution 11 overflows the surface of the embedding cassette 10, a problem during the slicing process may occur.

In the process of slicing the embedded tissue, fixation of the cassette, on which the paraffin solution including the tissue coagulates, to the slicing device and slicing of the fixed paraffin solution including the tissue are repeated and, thus, the tissue embedded in the paraffin solution may be sliced to a thickness necessary for biopsy.

Here, a slicing device 30 includes a fixing unit 31 to fix the embedding cassette and a position adjusting unit 32 to adjust the position of the fixing unit 31, as exemplarily shown in FIG. 3.

A slicing unit (not shown) to slice the coagulated paraffin on the embedding cassette 10 fixed to the slicing device 30 is provided on the front surface of the slicing device 30.

Therefore, the process of fixing the embedding cassette 10, on which the paraffin solution coagulates, to the slicing device 30 is very important when the tissue embedded in the coagulated paraffin is sliced.

If the paraffin solution coagulates under the condition that the paraffin solution 11 overflows the upper surface of the embedding cassette and the coagulated paraffin solution protrudes from the upper surface of the embedding cassette, as exemplarily shown in FIG. 2, the slicing device 30 requires a process of adjusting the embedding cassette 10.

That is, fixed states of an embedding cassette without a coagulated paraffin protrusion, an embedding cassette with a large-sized coagulated paraffin protrusion and an embedding cassette with a small-sized coagulated paraffin protrusion to the slicing device 30 are different, as exemplarily shown in FIG. 4.

Therefore, in order to perform an effective slicing operation, additional operations to fix the embedding cassettes of the respective states are required.

If the slicing device is not adjusted, an operation to remove the coagulated paraffin protrusion from the upper surface of the embedding cassette is required.

Further, in the conventional embedding assembly for biopsy used in the biopsy method, since the embedding cassette 10 is simply seated on the embedding mold 20, as exemplarily shown in FIG. 13, the paraffin solution 11 causes separation of the embedding cassette 10 from the embedding mold 20 and, thereby, a gap between the embedding cassette 10 and the embedding mold 20 is generated and the paraffin solution 11 leaks through the gap and overflows onto the side surfaces of the embedding cassette 10.

In such a state, when the paraffin solution 11 coagulates, the paraffin solution 11 on the side surfaces of the embedding cassette 10 coagulates, as exemplarily shown in FIG. 14.

Therefore, the conventional embedding assembly for biopsy may not be directly used in a subsequent process, i.e., the process of slicing the paraffin tissue block, and requires an additional operation to remove the coagulated paraffin from the side surfaces of the embedding cassette.

Conventionally, in order to remove the coagulated paraffin from the side surfaces of the embedding cassette, a flat panel apparatus for removal of paraffin at a high temperature (about 78° C. or more) using properties of paraffin is provided, and a user manually sears the coagulated paraffin on the side surfaces of the embedding cassette 10 with the flat panel apparatus for removal of paraffin at a high temperature, thus being capable of removing the coagulated paraffin from the side surfaces of the embedding cassette 10.

As another method, an automation apparatus for removal of paraffin is used but it is disadvantageous in that a user needs to directly insert the embedding cassette 10 with the coagulated paraffin on the side surfaces thereof into the automation apparatus for removal of paraffin and, thus, a long time is taken and the automation apparatus for removal of paraffin is expensive.

As yet another method, an operator removes the coagulated paraffin using a tool, such as a knife, and, in this case, a time of 5 to 7 seconds per embedding cassette is taken and the operator is in danger.

SUMMARY

Therefore, the present invention has been made in view of the above problems, and it is an object of the present invention to provide an embedding cassette which, even if a large amount of a paraffin solution is injected into the embedding cassette during an embedding process, discharges the paraffin solution exceeding a proper amount to the outside so that a designated amount of the paraffin solution may coagulate on the embedding cassette.

It is another object of the present invention to provide an embedding assembly for biopsy in which a barrier of a proper size is formed on an embedding mold and an embedding cassette is fixedly inserted into the barrier of the embedding mold so as to prevent a paraffin solution from flowing onto the side surfaces of the embedding cassette and thus from coagulating during an embedding process.

It is yet another object of the present invention to provide an embedding assembly for biopsy which prevents a paraffin solution from leaking to the outside of an embedding mold and thus from coagulating on the side surfaces of an embedding cassette during an embedding process.

In accordance with an aspect of the present invention, the above and other objects can be accomplished by the provision of an embedding cassette for biopsy to embed tissue received in an embedding mold provided with a space to receive the tissue when the embedding cassette is combined with the embedding mold, including a body provided with a space communicating with the receipt space of the combined embedding mold so that an injected paraffin solution may coagulate therein during embedding of the tissue and at least one paraffin barrier groove formed at the edge of the lower surface of the body, wherein, when the embedding cassette is combined with the embedding mold and embedding of the tissue is carried out, the injected paraffin solution flows into the at least one paraffin barrier groove and forms a barrier and, thereby, leakage of the paraffin solution between the embedding cassette and embedding mold is prevented.

At least one volume maintenance opening to discharge the paraffin solution exceeding a predetermined volume to the outside, even if more than the predetermined volume of the paraffin solution is injected, may be formed on the side surfaces of the body.

The at least one volume maintenance opening may be formed by bending the upper portions of the left/right side surfaces of the body.

On the other hand, the at least one volume maintenance opening may be formed on the left/right side surfaces of the body.

Further, the at least one volume maintenance opening may be formed by bending the upper portion of the rear surface of the body.

In accordance with another aspect of the present invention, there is provided an embedding mold for biopsy combined with an embedding cassette, having a body provided with a tissue receipt space to receive tissue and at least one rib fixing groove formed at the edge of the lower surface of the body, including a load part configured to receive the embedding cassette, at least one fixing rib formed on the load part and corresponding to the at least one rib fixing groove of the embedding cassette, paraffin discharge holes formed at the outside of the at least one fixing rib of the load part so as to discharge a paraffin solution to the outside, and a tissue fixing space configured to receive the processed tissue so that the paraffin solution injected via the embedding cassette coagulates under the embedding cassette under the condition that the embedding cassette is combined with the embedding mold through the at least one fixing rib.

Subsidiary paraffin discharge holes to discharge the paraffin solution to the outside may be formed at the inner corners of the load part adjacent to the at least one fixing rib.

Guide protrusions to guide insertion of the embedding cassette may be formed at one side of the at least one fixing rib and guide grooves may be formed in the at least one rib fixing groove of the embedding cassette.

The at least one rib fixing groove of the embedding cassette may be an integrated rib fixing groove formed at one side of the edge of the embedding cassette and the at least one fixing rib of the embedding mold may be an integrated fixing rib formed at one side of the edge of the embedding mold.

The embedding mold for biopsy may further include insertion grooves configured to partially accommodate the side surfaces of the embedding cassette.

In accordance with yet another aspect of the present invention, there is provided an embedding assembly for biopsy including an embedding cassette including a body provided with a tissue receipt space to receive tissue and at least one rib fixing groove formed at the edge of the lower surface of the body, and an embedding mold including a load part configured to receive the embedding cassette, at least one fixing rib formed on the load part and corresponding to the at least one rib fixing groove of the embedding cassette, and a tissue fixing space configured to receive processed tissue so that the paraffin solution injected via the embedding cassette coagulates under the embedding cassette under the condition that the embedding cassette is combined with the embedding mold through the at least one fixing rib.

Paraffin discharge holes to discharge the paraffin solution to the outside may be formed at the outside of the at least one fixing rib of the load part.

Further, subsidiary paraffin discharge holes to discharge the paraffin solution to the outside may be formed at the inner corners of the load part adjacent to the at least one fixing rib.

Further, guide protrusions to guide insertion of the embedding cassette may be formed at one side of the at least one fixing rib and guide grooves may be formed in the at least one rib fixing groove of the embedding cassette.

The at least one rib fixing groove of the embedding cassette may be an integrated rib fixing groove formed at one side of the edge of the embedding cassette and the at least one fixing rib of the embedding mold may be an integrated fixing rib formed at one side of the edge of the embedding mold.

The embedding mold 200 may further include insertion grooves 260, configured to partially accommodate the side surfaces of the embedding cassette, and outer walls 270.

As described above, in accordance with the present invention, an embedding cassette is provided with paraffin barrier grooves and combined with en embedding mold, thus preventing a paraffin solution from overflowing onto the side surfaces of the embedding cassette and coagulating on the side surfaces of the embedding cassette during an embedding process, and executing a slicing process just after the embedding process without removal of the coagulated paraffin from the side surfaces of the embedding cassette.

Further, since the paraffin solution injected into an embedding mold is not coagulated under the condition that a coagulated paraffin protrusion is formed on the embedding cassette during the embedding process, the embedding cassette may be fed directly to a slicing device without any separate operation, a biopsy time may be reduced and an inspection process may be simplified.

Further, rib fixing grooves are formed on the embedding cassette, fixing ribs are formed on the embedding mold, and the embedding cassette and the embedding mold are combined through the rib fixing grooves and the fixing ribs, thus preventing the paraffin solution from overflowing onto the side surfaces of the embedding cassette and coagulating on the side surfaces of the embedding cassette during the embedding process, and executing the slicing process just after the embedding process without removal of the coagulated paraffin from the side surfaces of the embedding cassette.

Further, the slicing process is carried out without any additional operation for removing the coagulated paraffin from the side surfaces of the embedding cassette and thus, the biopsy time may be reduced and the inspection process may be simplified.

Moreover, paraffin discharge holes are formed at the outside of the fixing ribs of a load part and, thus, even if the paraffin solution overflows the embedding mold, the overflowed paraffin solution is discharged to the outside through the paraffin discharge holes, thereby preventing the paraffin solution from coagulating on the side surfaces of the embedding cassette.

DESCRIPTION OF DRAWINGS

FIG. 2 shows views illustrating a state in which a paraffin solution is embedded in the conventional embedding cassette using the convention embedding cassette and embedding mold of FIG. 1.

FIG. 4 shows views illustrating the embedding cassette fixed to the slicing device after the embedding operation shown in FIG. 1.

DETAILED DESCRIPTION

Embodiment 1

Hereinafter, an embedding cassette for biopsy in accordance with one embodiment of the present invention will be described in detail with reference to FIGS. 5 to 11.

One embodiment of the present invention relates to an embedding cassette which forms a space to receive tissue within an embedding mold and embeds the tissue received in the embedding mold.

Figure 1:
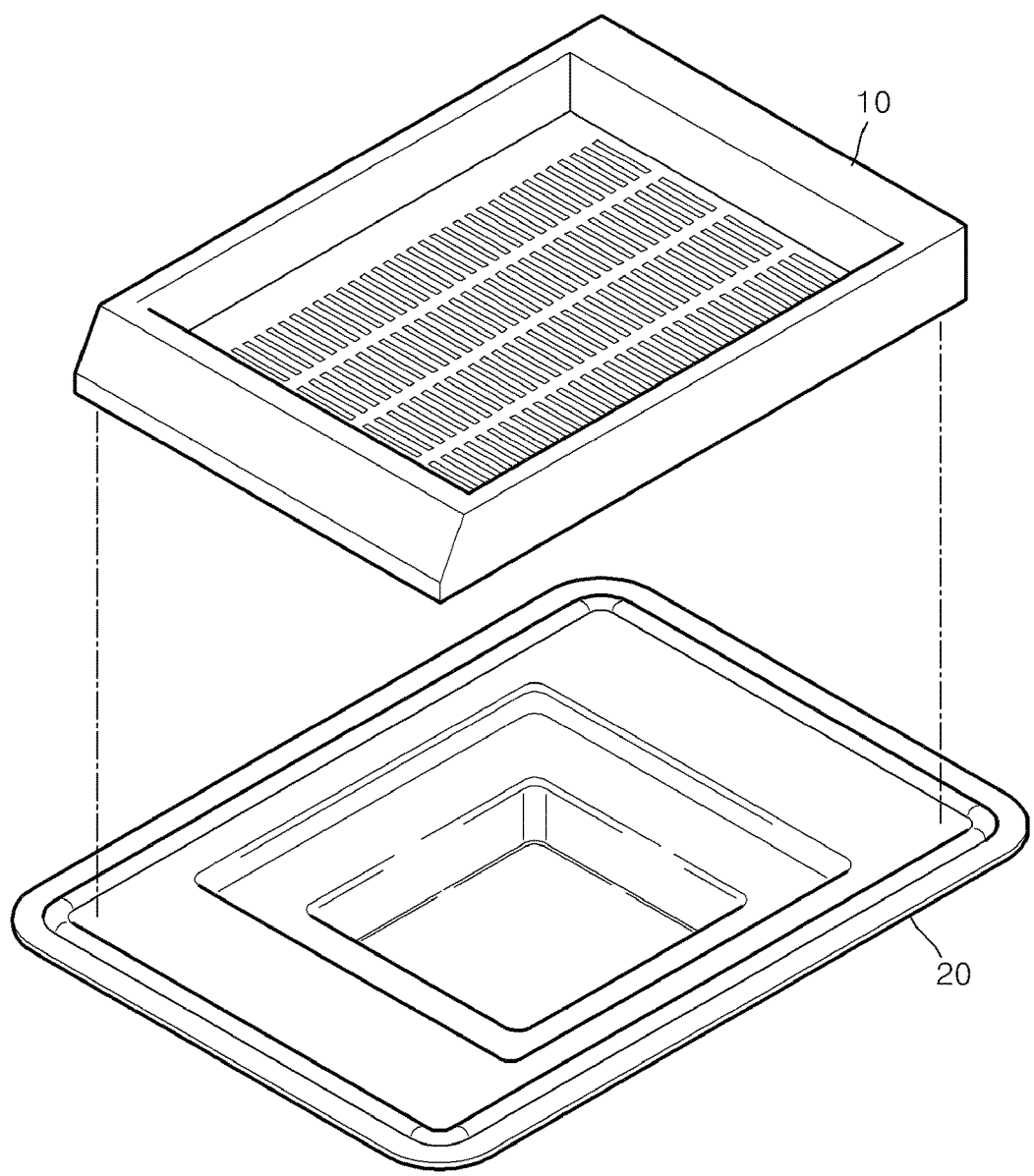
FIG. 1 is an exploded perspective view illustrating a conventional embedding cassette and a conventional embedding mold for biopsy used in a biopsy method.
Figure 3:
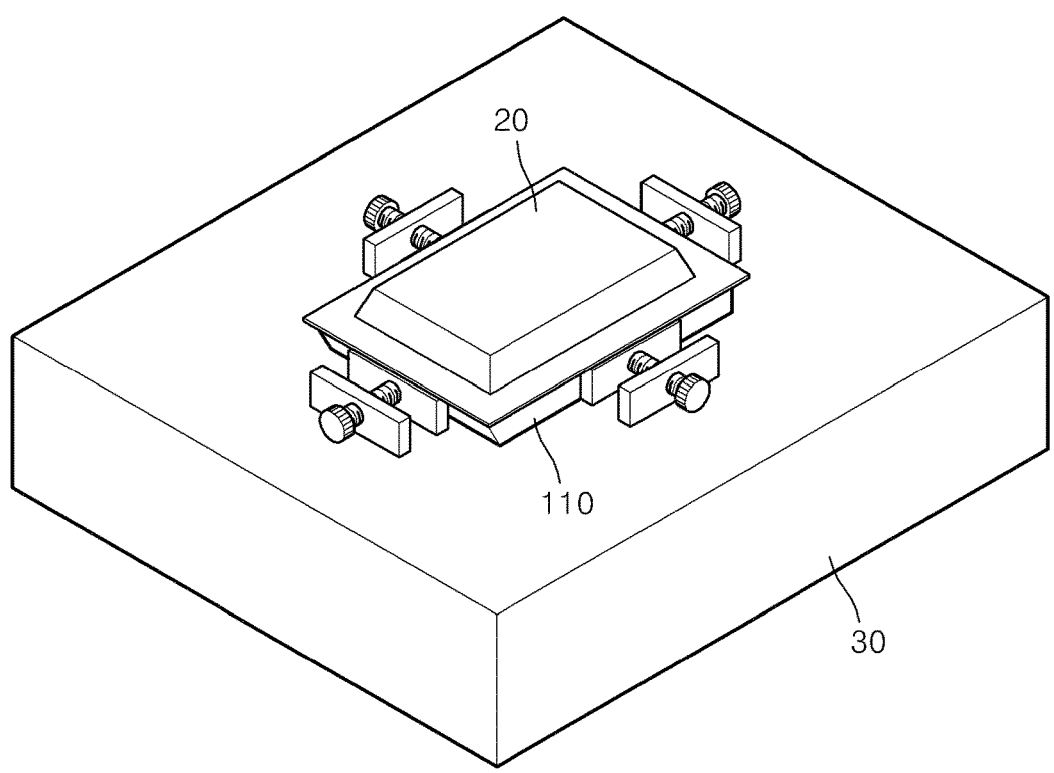
FIG. 3 is a view illustrating the embedding cassette of FIG. 1 fixed to a slicing device.
Figure 5:
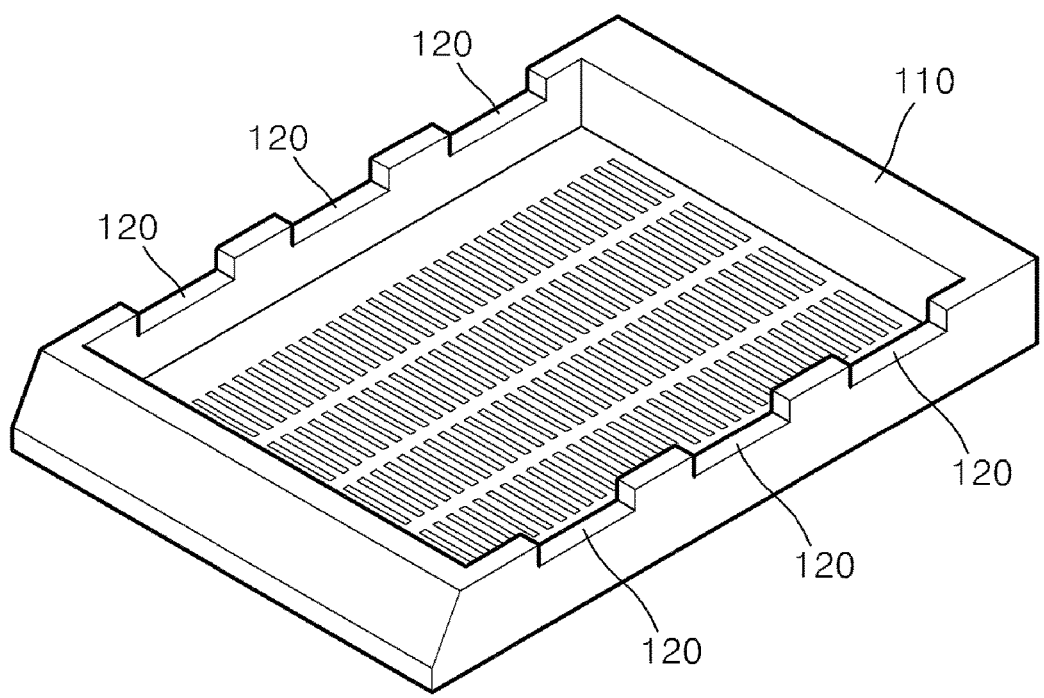
FIG. 5 is a perspective view illustrating an embedding cassette in accordance with the present invention.
Figure 6:
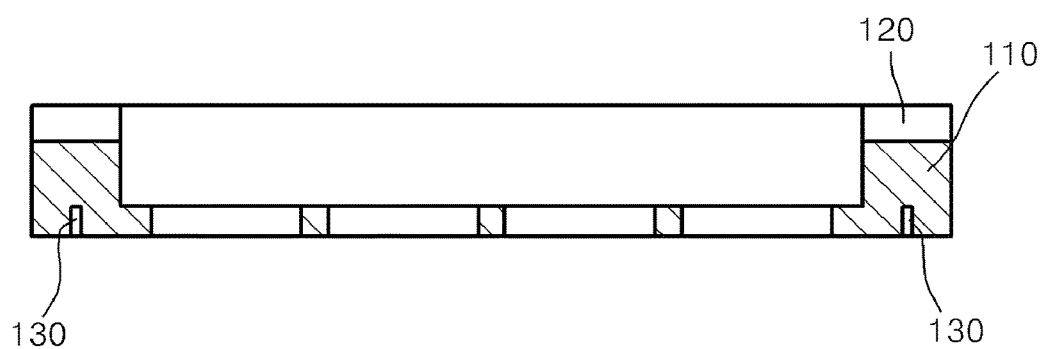
FIG. 6 is a cross-sectional view of the embedding cassette of FIG. 5.
Figure 7:
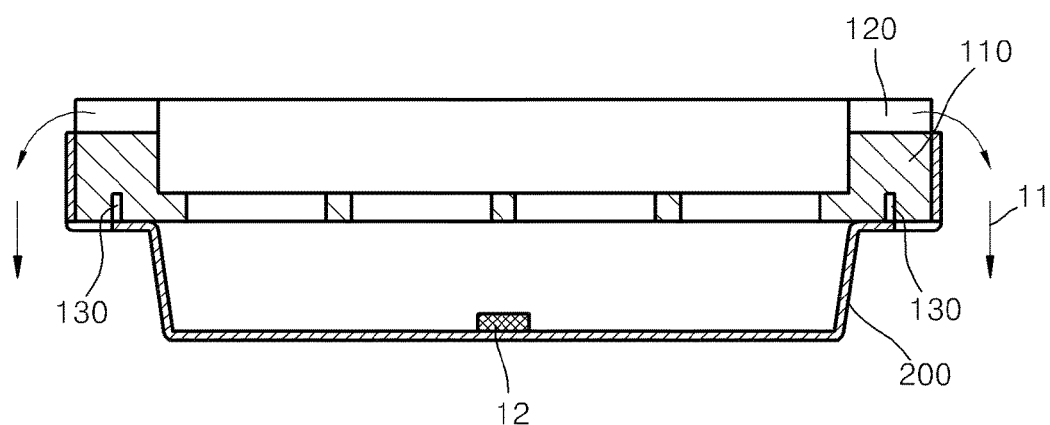
FIGS. 7 to 9 are reference views illustrating an embedding process using paraffin with the embedding cassette in accordance with the present invention.
Figure 8:
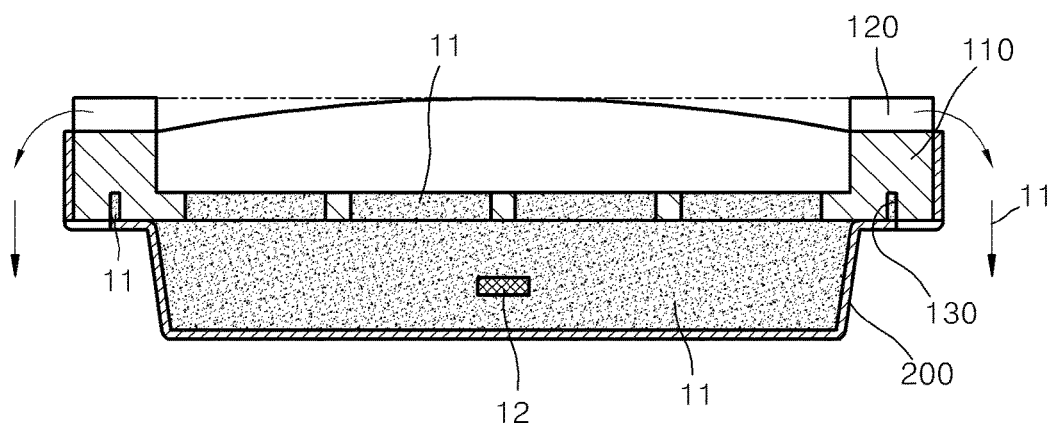
Figure 9:
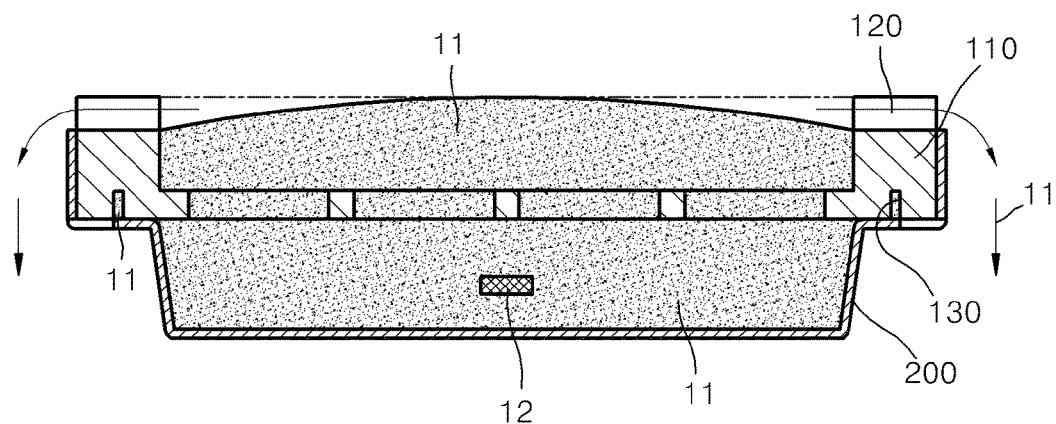

FIG. 5 is a perspective view illustrating an embedding cassette for biopsy in accordance with the present invention, FIG. 6 is a cross-sectional view of the embedding cassette for biopsy of FIG. 5, and reference numerals in the present invention are restricted to FIGS. 5 to 11.

The embedding cassette in accordance with the present invention includes a body 111, volume maintenance openings 120 and paraffin barrier grooves 130.

A space which communicates with a receipt space of an embedding mold 200 so that an injected paraffin solution 11 may coagulate in the space during an embedding process may be formed in the body 111. A space to receive tissue 12 so as to perform processing of the tissue 12 may be formed in the body 110, a known selective transmitting member (represented by no reference numeral) which allows the paraffin solution 11 to pass therethrough while preventing the tissue 12 from escaping to the outside may be formed at the lower portion of the body 110, and a lid provided with a selective transmitting member may be detachably attached to the body 110.

At least one volume maintenance opening 120 is formed on the side surfaces of the body 110 and discharges more than a predetermined amount of the paraffin solution 11 to the outside, even if more than the predetermined amount of the paraffin solution 11 is injected into the body 110, so as to prevent the paraffin solution 11 from coagulating under the condition that a coagulated paraffin protrusion is formed on the body 110.

FIG. 6 is a cross-sectional view of the embedding cassette of FIG. 5, and at least one paraffin barrier groove 130 may be formed on the body 110 of the embedding cassette along the edge of the lower surface of the body 110./Therefore, the paraffin barrier grooves 130 formed on the lower surface of the embedding cassette may prevent the paraffin solution 11, injected through the embedding cassette under the condition that the embedding cassette and the embedding mold 200 are combined, from leaking between the embedding cassette and the embedding mold 200 and coagulating on the side surfaces of the embedding cassette.

By preventing the paraffin solution 11 from leaking between the embedding cassette and the embedding mold 200 and coagulating on the side surfaces of the embedding cassette through the paraffin barrier grooves 130, even if a predetermined amount of the paraffin solution 11 exceeds the volume of the embedding cassette combined with the embedding mold 200, the paraffin solution 11 may not leak between the embedding mold 200 and the embedding cassette and may be discharged to the outside through the volume maintenance openings 120 formed on the body 110 of the embedding cassette.

The embedding process using the embedding cassette will be described. First, after the tissue 12 is received in the embedding mold 200, the embedding cassette is combined with the embedding mold 200, as exemplarily shown in FIG. 7.

Thereafter, the paraffin solution 11 is injected between the embedding mold 200 and the embedding cassette under the condition that the embedding mold 200 and the embedding cassette are combined. Here, when the paraffin solution 11 is injected between the embedding mold 200 and the embedding cassette, as exemplarily shown in FIG. 8, the paraffin solution 11 is injected into the paraffin barrier grooves 130 and coagulates.

If the paraffin solution 11 is injected into the paraffin barrier grooves 130 and coagulates, the paraffin solution 11 coagulated in the paraffin barrier grooves 130 may prevent the injected paraffin solution 11 from leaking between the embedding cassette and the embedding mold 200 and the paraffin solution 11 exceeding the predetermined amount may be discharged to the outside through the volume maintenance openings 120, thus being capable of preventing the paraffin solution from coagulating into a protrusion shape on the body 110 of the embedding cassette.

Figure 10:
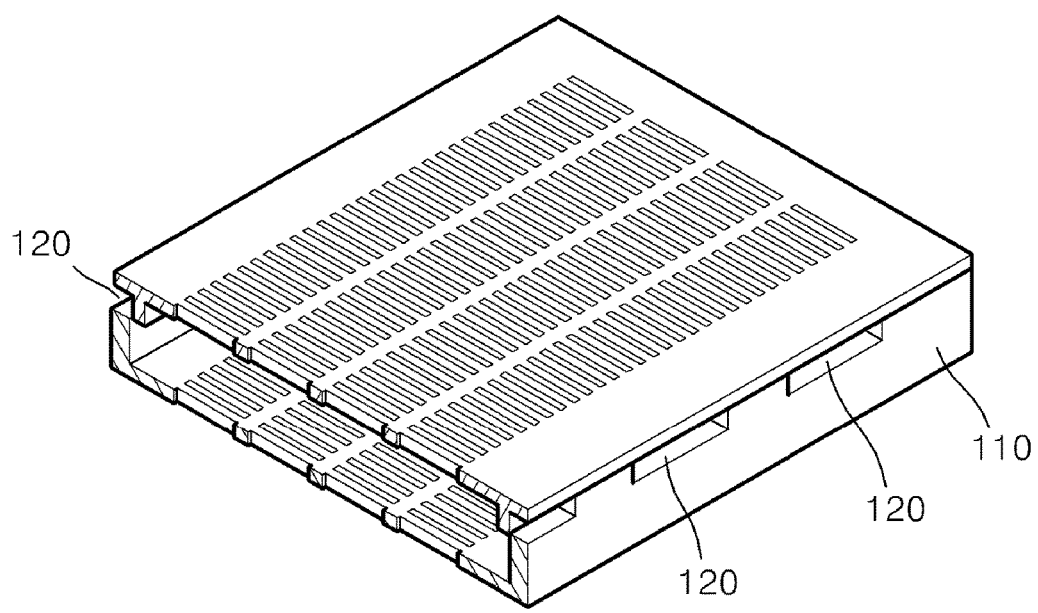
FIG. 10 is a cross-sectional view illustrating the embedding cassette of FIG. 5 combined with a lid.

Such a body 110 of the embedding cassette may be coupled with a lid (represented by no reference numeral), as exemplarily shown in FIG. 10, and used during the processing process.

Figure 11:
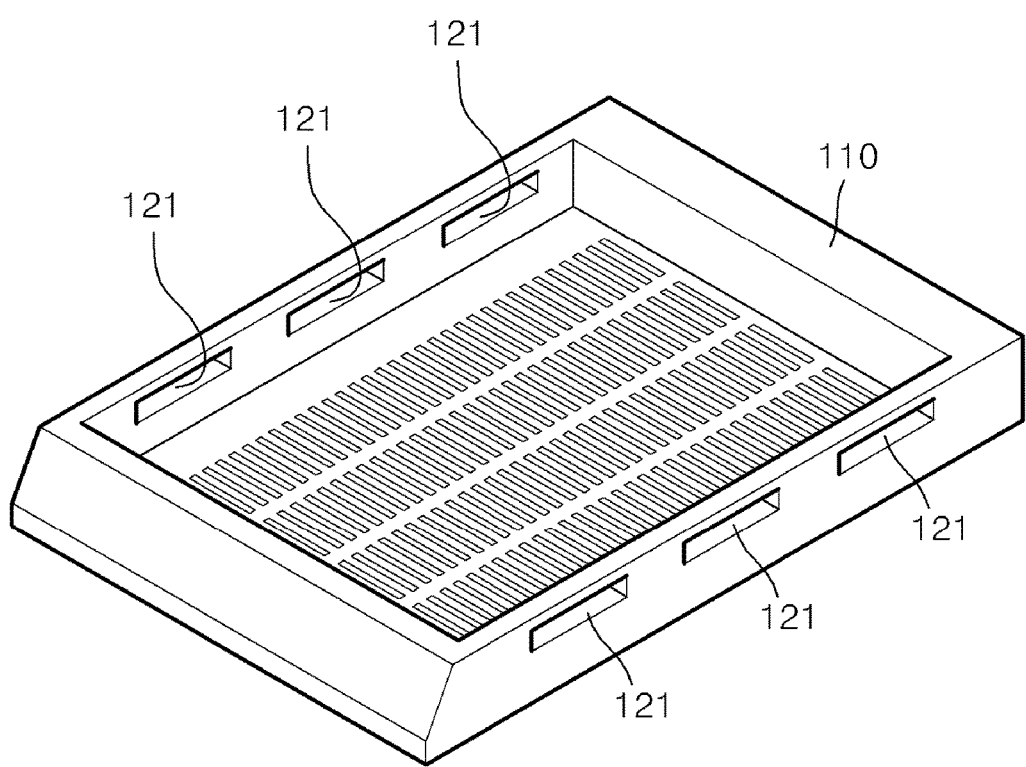
FIG. 11 is a perspective view illustrating an embedding cassette in accordance with another embodiment of the present invention.

In accordance with another embodiment, volume maintenance openings 121 having a hole shape may be formed on left/right side surfaces of the body 11, as exemplarily shown in FIG. 11.

If the volume maintenance openings 121 having a hole shape are formed on left/right side surfaces of the body 11, as exemplarily shown in FIG. 11, convenience in a manufacturing process may be provided and, even though a lid is combined with the embedding cassette, closing of the volume maintenance openings 121 with the lid may be prevented. Therefore, a conventional paraffin lid may be easily used.

In addition, the volume maintenance openings 121 may be formed by bending the upper portion of the rear surface of the body 110, although this is not shown in the drawings. If the volume maintenance openings 121 are formed by bending the upper portion of the rear surface of the body 110, the paraffin solution 11 is discharged to the outside through the rear surface of the body 110 so that coagulation of the paraffin solution 11 on the side surfaces of the body 110 may be prevented, and the embedding cassette is mounted on a slicing device without any separate operation so that a slicing process may be carried out.

The paraffin barrier grooves 130 may be formed to have an embossed shape but is not limited thereto. Therefore, various kinds of embedding cassettes may be manufactured.

Figure 12:
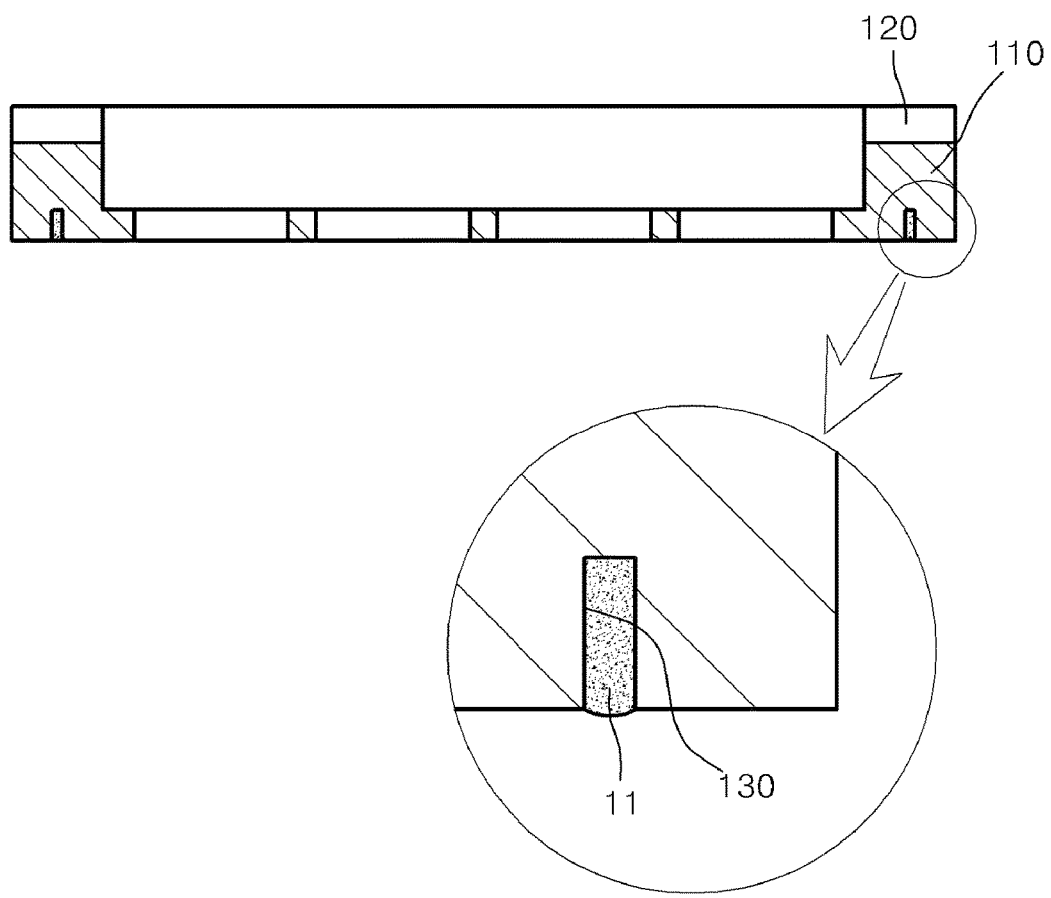
FIG. 12 is a view illustrating a state in which a paraffin barrier groove of the embedding cassette of FIG. 5 is filled with a paraffin solution.
Figure 13:
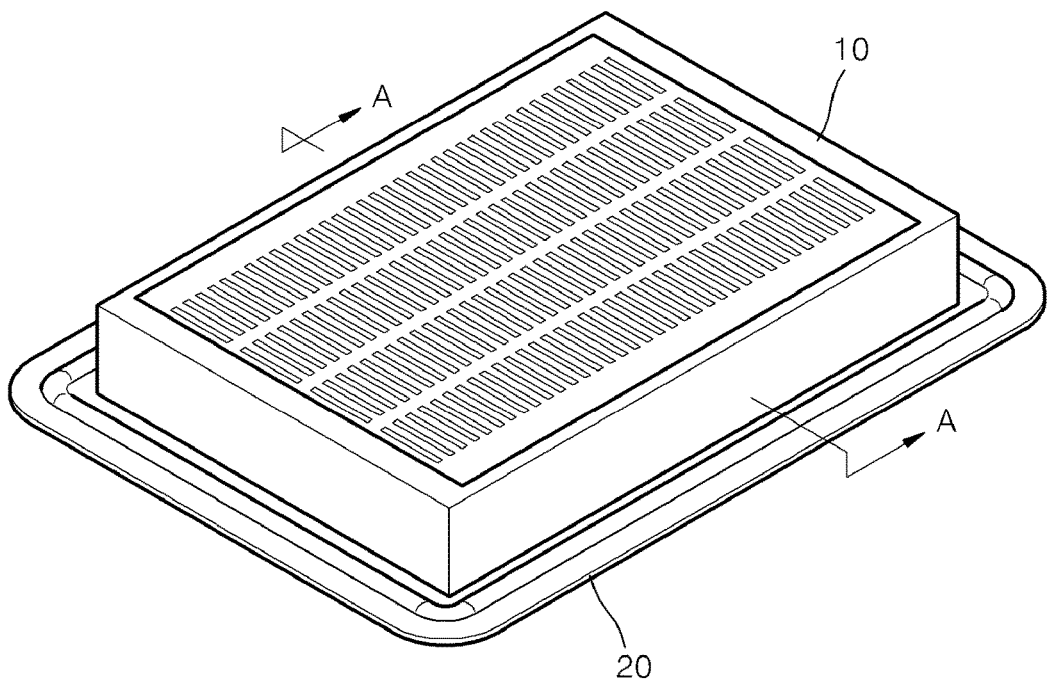
FIG. 13 is an assembled view of a conventional biopsy equipment set of FIG. 1.
Figure 14:
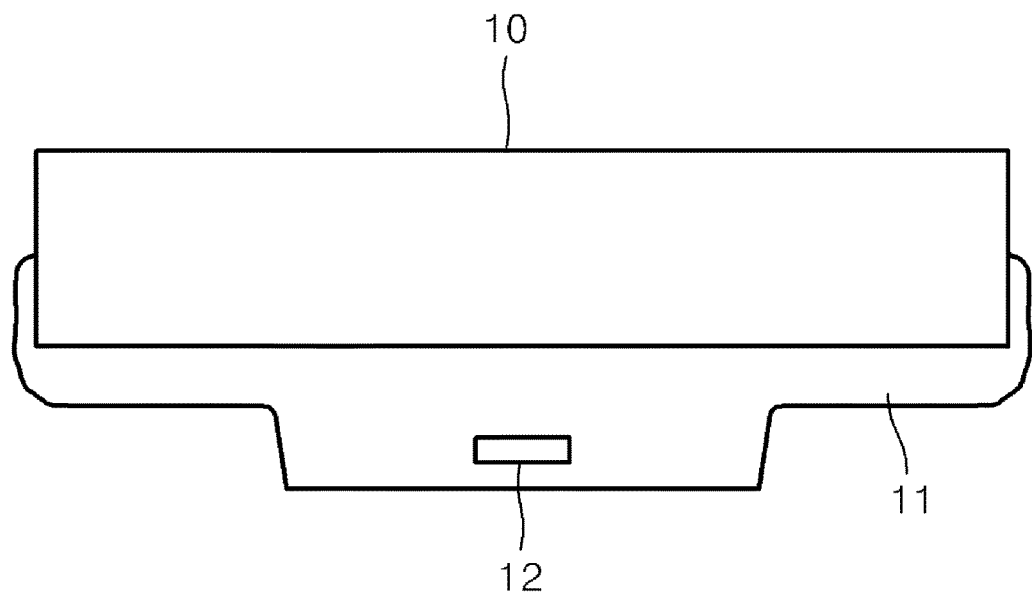
FIG. 14 is a cross-sectional view illustrating coagulation of the paraffin solution on the embedding cassette.

Further, another embedding process using the embedding cassette will be described. First, after tissue 12 is received in the embedding mold 200, the embedding cassette is soaked in a paraffin solution before the embedding cassette is combined with the embedding mold 200, as exemplarily shown in FIG. 7. If the embedding cassette is soaked in the paraffin solution and then taken out of the paraffin solution, the paraffin barrier grooves 130 of the embedding cassette are filled with the paraffin solution, as exemplarily shown in FIG. 12, and thereafter, serve as paraffin barriers when the embedding cassette is combined with the embedding mold 200.

When the embedding cassette and the embedding mold 200 are combined under the condition that the paraffin barrier grooves 130 of the embedding cassette are filled with the paraffin solution, the paraffin barriers are formed in the paraffin barrier grooves 130 and may prevent the paraffin solution from leaking between the embedding mold 200 and the embedding cassette during the embedding process after combination of the embedding cassette with the embedding mold 200. Thereafter, the embedding process may be performed through the same method as in the above-described embodiment.

Embodiment 2

An embedding mold and an embedding assembly in accordance with another embodiment of the present invention will be described in detail with reference to FIGS. 15 to 19, and reference numerals are also restricted to FIGS. 15 to 19.

Figure 15:
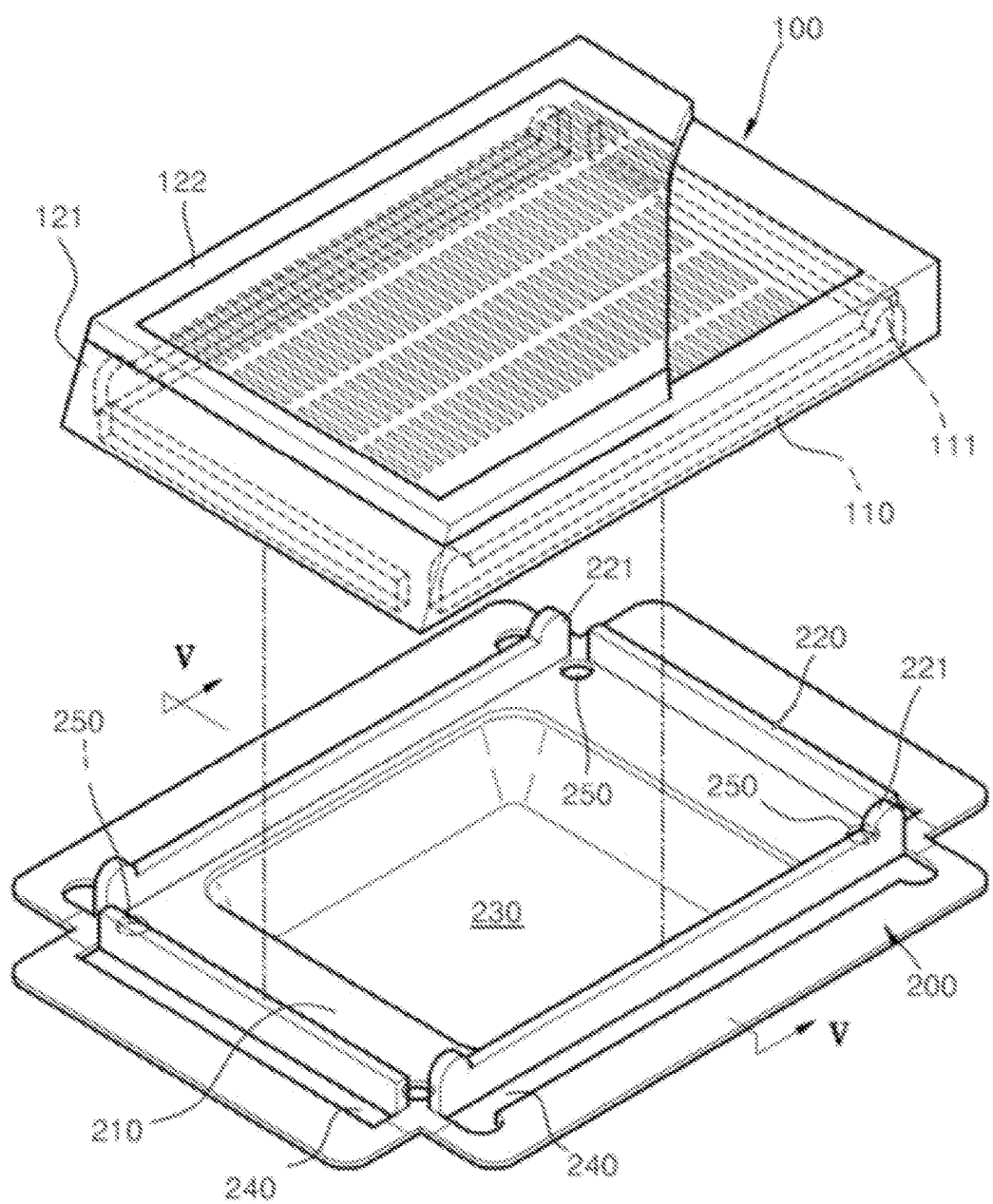
FIG. 15 is an exploded perspective view illustrating an embedding assembly including an embedding cassette for biopsy and an embedding mold combined with the embedding cassette in accordance with another embodiment of the present invention.
Figure 16:
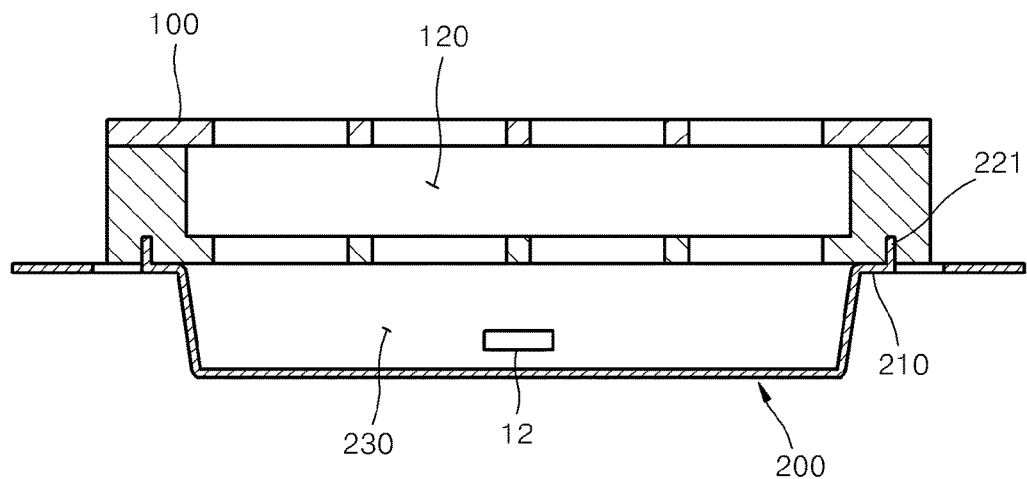
FIG. 16 is a cross-sectional view of the embedding mold assembled with the embedding cassette for biopsy of FIG. 15.
Figure 17:
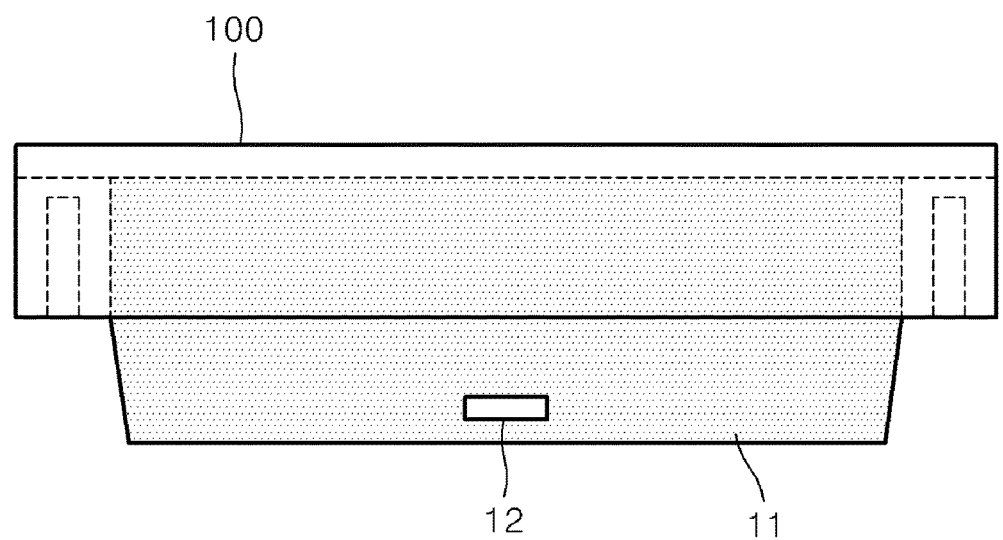
FIG. 17 is a cross-sectional view illustrating coagulation of a paraffin solution on the embedding cassette of the embedding assembly for biopsy of FIG. 15.

FIG. 15 is an exploded perspective view illustrating an embedding assembly including an embedding cassette for biopsy and an embedding mold combined with the embedding cassette in accordance with the present invention, and FIG. 16 is a cross-sectional view of the embedding mold assembled with the embedding cassette for biopsy of FIG. 15.

The embedding assembly for biopsy in accordance with this embodiment of the present invention includes an embedding cassette 100 and an embedding mold 200.

The embedding cassette 100 includes a body 121 having a tissue receipt space 120 to receive tissue 12, a lid 122 to cover the tissue receipt space 120, and at least one rib fixing groove 110 formed at the edge of the lower surface of the body 121.

A selective transmitting member which allows a paraffin solution 11 to pass therethrough while preventing the tissue 12 from escaping to the outside may be formed at the lower portion of the body 121 of the embedding cassette 100, and the tissue receipt space 120 to receive the tissue 12 may be provided within the body 121.

The lid 122 may be provided with a selective transmitting member which allows the paraffin solution 11 to pass therethrough while preventing the tissue 12 from escaping to the outside may be formed on the lid 122 of the embedding cassette 100 and cover the tissue receipt space 120 of the body 121.

Further, the at least one rib fixing groove 110 may be formed along the edge of the lower surface of the body 121 of the embedding cassette 100.

Such an embedding cassette 100 is used during the processing and slicing processes of the tissue 12. During the processing process, after the tissue is received in the body 121 of the embedding cassette 100 so that the paraffin solution is absorbed by the tissue, the body 121 is covered with the lid 122, and the embedding cassette 100 is labeled and put into a processing device.

Thereafter, the embedding cassette 100 is used during the embedding process. For this purpose, the processed tissue is taken out of the embedding cassette 100 and put into a tissue fixing space 230 of the embedding mold 200, and the embedding mold 200 and the embedding cassette 100 are combined. Here, the embedding cassette 100 is inserted into fixing ribs 220 of the embedding mold 200, thus being fixed. Thereafter, the paraffin solution in a liquid state is injected into the tissue fixing space 230 of the embedding mold 200 through the embedding cassette 100 and, after a designated time has passed, the paraffin solution 11 together with the processed tissue 12 coagulates under the embedding cassette 100. Here, the lid 122 of the embedding cassette 100 is not connected with such an operation.

The embedding mold 200 of the embedding assembly for biopsy in this embodiment of the present invention may include a load part 210, the fixing ribs 220 and the tissue fixing space 230.

The load part 210 of the embedding mold 200 serves to receive the embedding cassette 100 thereon.

At least one fixing rib 220 corresponding to the at least one rib fixing groove 110 of the embedding cassette 100 is formed on the load part 210. The fixing ribs 220 are inserted into the rib fixing grooves 110 of the embedding cassette 100 so as to fix the embedding cassette 110 and prevent the paraffin solution from overflowing and coagulating on the side surfaces of the embedding cassette 100 during the embedding process. Here, the rib fixing grooves of the embedding cassette 100 and the fixing ribs of the embedding mold 200 may be interchanged.

The tissue fixing space 230 serves to receive the processed tissue 12 and to allow the paraffin solution 11, injected into the tissue fixing space 230 via the embedding cassette 110, to coagulated under the embedding cassette 100 under the condition that the embedding cassette 100 is combined with the embedding mold 200 through the fixing ribs.

In accordance with this embodiment of the present invention, the embedding cassette 100 is fixed by inserting the fixing ribs 220 of the embedding mold 200 into the rib fixing grooves 110 of the embedding cassette 100.

Thereafter, the processed tissue 12, received in the tissue fixing space 230 of the embedding mold 200, together with the paraffin solution 11 injected through the embedding cassette 100 coagulates under the embedding cassette 100.

Here, the rib fixing grooves 110 of the embedding cassette 100 and the fixing ribs 220 prevent the paraffin solution 11 from leaking or flowing to the outside and, thus, the paraffin solution 11 does not coagulate on the side surfaces of the embedding cassette 100 but coagulates only under the embedding cassette 100.

The embedding cassette 100 may be mounted on a microtome to slice the coagulated tissue 12 together with the paraffin solution 11 without a separate process of removing the coagulated paraffin solution 11 from the side surfaces of the embedding cassette 100 and, thus, the process of slicing the coagulated paraffin solution 11 under the embedding cassette 110 may be performed.

Further, in this embodiment of the present invention, paraffin discharge holes 240 to discharge the paraffin solution 11 to the outside may be respectively formed at the outside of the fixing ribs 220 of the load part 210. If the paraffin discharge holes 240 are formed at the outside of the fixing ribs 220 of the load part 210, even though the paraffin solution 11 overflows the embedding cassette 100, the paraffin solution 11 is discharged to the outside through the paraffin discharge holes 240 and, thus, coagulation of the paraffin solution 11 on the side surfaces of the embedding cassette 100 may be prevented.

Further, in this embodiment of the present invention, subsidiary paraffin discharge holes 250 to discharge the excessively provided paraffin solution 11 to the outside may be formed at the inner corners of the load part 210 adjacent to the fixing ribs 220. Further, subsidiary discharge holes (not shown) for the cassette may be formed at positions of the embedding cassette 100 corresponding to the subsidiary paraffin discharge holes 250 when the embedding cassette 100 is combined with the embedding mold 200. Therethrough, provision of the paraffin solution 11 may be adjusted so that a proper amount of the paraffin solution 11 may be used, and coagulation of the paraffin solution 11 on the side surfaces of the embedding cassette 100 may be prevented.

Further, the subsidiary paraffin discharge holes 250 may serve to conveniently separate the embedding cassette 100 and the embedding mold 200 from each other after the embedding process by inserting an arbitrary tool into the subsidiary paraffin discharge holes 250.

Moreover, in this embodiment of the present invention, guide protrusions 221 to guide insertion of the embedding cassette 100 may be formed at one side of the fixing ribs 220, and guide grooves 111 may be formed in the rib fixing grooves 110 of the embedding cassette 100. These structures may simplify combination between the embedding cassette and the embedding mold 200.

Further, an embedding assembly in accordance with another embodiment of the present invention has the same components as the embedding assembly in accordance with the former embodiment except for a rib fixing groove 110 of an embedding cassette and a fixing rib 220.

The rib fixing groove 110 of the embedding cassette may be an integrated rib fixing groove formed at one side of the edge of the embedding cassette and the fixing rib 220 of the embedding mold 200 may be an integrated fixing rib formed at one side of the edge of the embedding mold 200. Therefore, this embodiment of the present invention may be implemented through various manufacturing methods.

Figure 18:
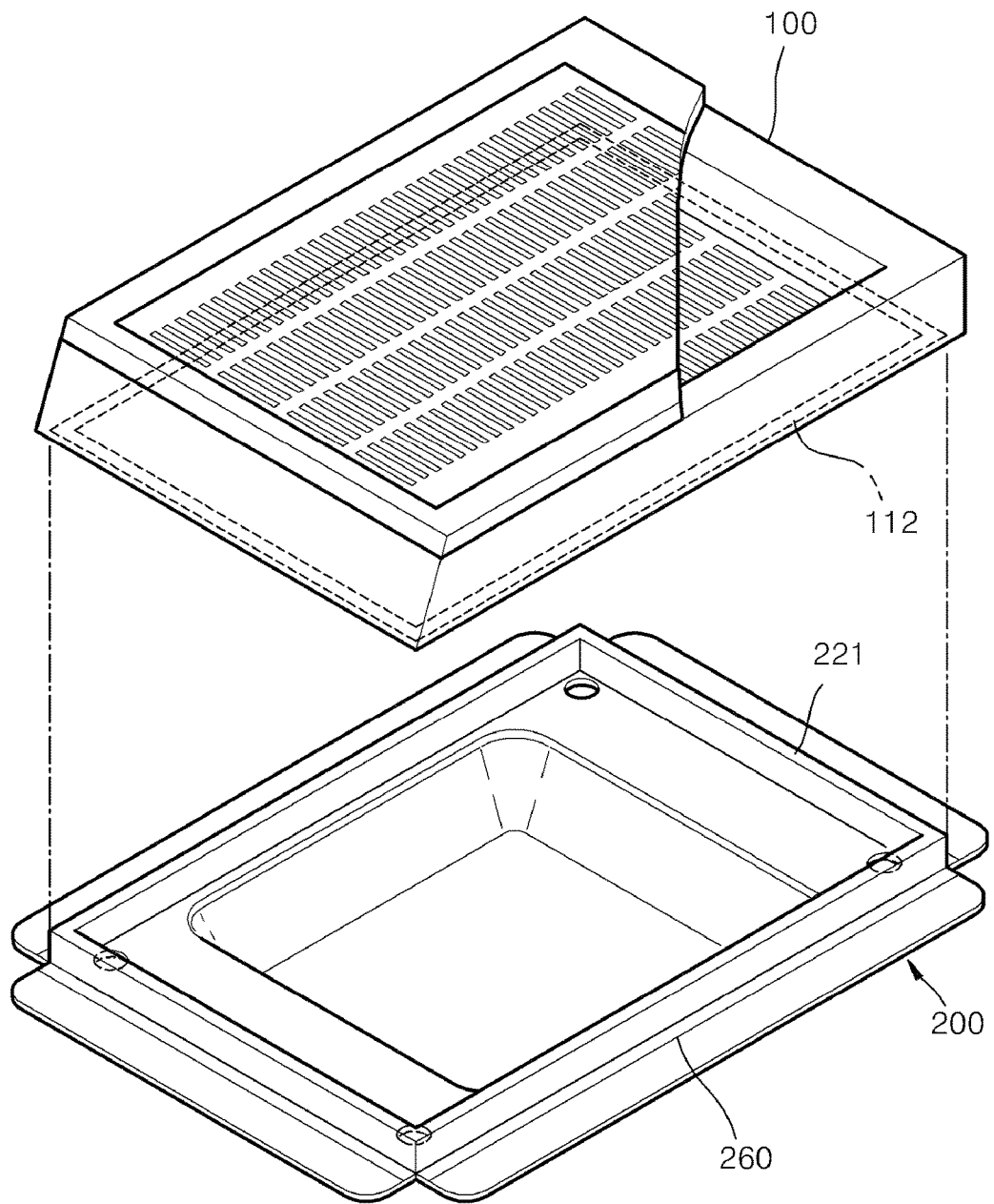
FIG. 18 is an exploded perspective view illustrating the embedding cassette for biopsy in accordance with another embodiment of the present invention and an embedding mold having another shape and assembled therewith.

Although FIG. 18 illustrates that only subsidiary paraffin discharge holes 250 are formed on the embedding mold 200 without paraffin discharge holes 240 formed at the outside of the fixing rib 220, paraffin discharge holes 240 and subsidiary paraffin discharge holes 250 may be selectively formed according to manufacturing methods of the embedding mold 200.

Figure 19:
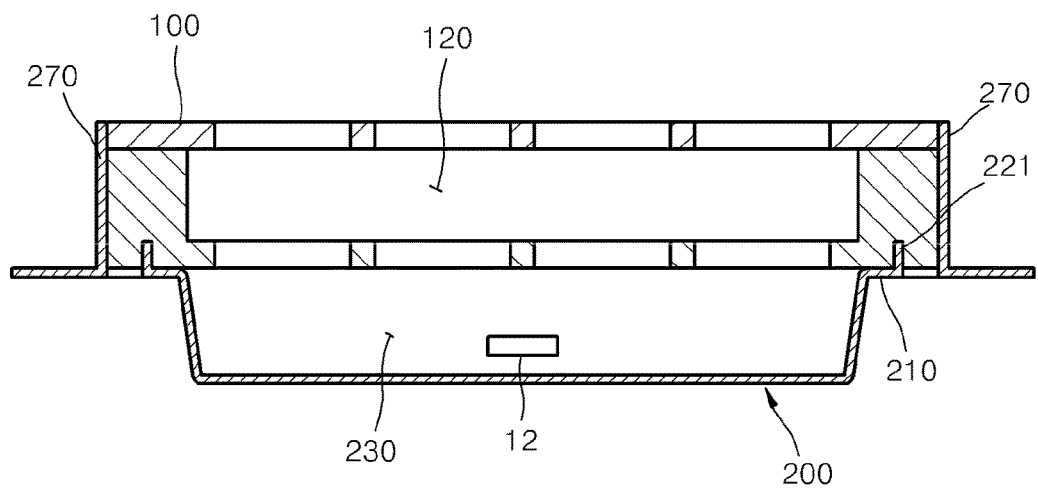
FIG. 19 is a cross-sectional view of the embedding mold assembled with the embedding cassette for biopsy of FIG. 18.

FIG. 19 is a cross-sectional view of the embedding assembly for biopsy in accordance with this embodiment of the present invention. As exemplarily shown in FIG. 19, the embedding mold 200 includes insertion grooves 260, into which the side surfaces of the embedding cassette 100 are partially inserted, and may thus completely prevent coagulation of the paraffin solution on the side surfaces of the embedding cassette 100. Here, an outer wall 270 at one side of the insertion groove 260 has a height which is greater than or equal to the height of the side surfaces and the rear surface of the embedding cassette 100 but the present invention is not limited thereto.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An embedding mold for biopsy combined with an embedding cassette, having a body provided with a tissue receipt space to receive tissue and at least one rib fixing groove formed at the edge of the lower surface of the body, comprising:
   a load part configured to receive the embedding cassette;
   at least one fixing rib formed on the load part and corresponding to the at least one rib fixing groove of the embedding cassette;
   paraffin discharge holes formed at the outside of the at least one fixing rib of the load part so as to discharge a paraffin solution to the outside; and
   a tissue fixing space configured to receive the processed tissue so that the paraffin solution injected via the embedding cassette coagulates under the embedding cassette under the condition that the embedding cassette is combined with the embedding mold through the at least one fixing rib.

2. The embedding mold for biopsy according to claim 1, wherein subsidiary paraffin discharge holes to discharge the paraffin solution to the outside are formed at the inner corners of the load part adjacent to the at least one fixing rib.

3. The embedding mold for biopsy according to claim 1, wherein:
   guide protrusions to guide insertion of the embedding cassette are formed at one side of the at least one fixing rib; and
   guide grooves are formed in the at least one rib fixing groove of the embedding cassette.

4. The embedding mold for biopsy according to claim 1, wherein the at least one rib fixing groove of the embedding cassette is an integrated rib fixing groove formed at one side of the edge of the embedding cassette and the at least one fixing rib of the embedding mold is an integrated fixing rib formed at one side of the edge of the embedding mold.

5. The embedding mold for biopsy according to claim 4, further comprising insertion grooves configured to partially accommodate the side surfaces of the embedding cassette.

6. An embedding assembly for biopsy comprising:
   an embedding cassette including a body provided with a tissue receipt space to receive tissue and at least one rib fixing groove formed at the edge of the lower surface of the body; and
   an embedding mold including a load part configured to receive the embedding cassette, at least one fixing rib formed on the load part and corresponding to the at least one rib fixing groove of the embedding cassette, and a tissue fixing space configured to receive processed tissue so that the paraffin solution injected via the embedding cassette coagulates under the embedding cassette under the condition that the embedding cassette is combined with the embedding mold through the at least one fixing rib.

7. The embedding assembly for biopsy according to claim 6, wherein paraffin discharge holes to discharge the paraffin solution to the outside are formed at the outside of the at least one fixing rib of the load part.

8. The embedding assembly for biopsy according to claim 7, wherein subsidiary paraffin discharge holes to discharge the paraffin solution to the outside are formed at the inner corners of the load part adjacent to the at least one fixing rib.

9. The embedding assembly for biopsy according to claim 6, wherein:
   guide protrusions to guide insertion of the embedding cassette are formed at one side of the at least one fixing rib; and
   guide grooves are formed in the at least one rib fixing groove of the embedding cassette.

10. The embedding assembly for biopsy according to claim 6, wherein the at least one rib fixing groove of the embedding cassette is an integrated fib fixing groove formed at one side of the edge of the embedding cassette and the at least one fixing rib of the embedding mold is an integrated fixing rib formed at one side of the edge of the embedding mold.

11. The embedding assembly for biopsy according to claim 10, wherein the embedding mold further includes insertion grooves, configured to partially accommodate the side surfaces of the embedding cassette, and outer walls.

12. The embedding assembly for biopsy according to claim 6, wherein the embedding cassette further includes a lid configured to cover the tissue receipt space.

13. An embedding mold for biopsy combined with an embedding cassette, comprising:
   a load part to receive the embedding cassette, the load comprising a bottom, a side wall defining a tissue fixing space with the bottom, and at least one horizontal rib horizontally extended from the side wall;
   at least one fixing rib formed vertically on the at least one horizontal rib of the load part; and
   at least one paraffin discharge hole formed in the at least one horizontal rib at an outside of the at least one fixing rib of the load part so as to discharge an excessive paraffin solution to an outside of the tissue fixing space.

14. The embedding mold of claim 13, wherein a side wall comprises four side walls extended from the bottom;
   the at least one horizontal rib comprises four horizontal ribs each from each side wall;
   the at least one fixing rib comprises four fixing ribs each formed vertically on each horizontal rib; and
   the at least one paraffin discharge hole comprises four paraffin discharge holes each formed in each horizontal rib, four paraffin discharge holes.

15. The embedding mold of claim 13, wherein the at least one fixing rib of the embedding mold is an integrated fixing rib formed vertically on the at least one horizontal rib of the load part.

16. An embedding assembly comprising:
   an embedding cassette including a body provided with a tissue receipt space to receive tissue and at least one rib fixing groove formed at the edge of the lower surface of the body; and
   the embedding mold of claim 13.

17. The embedding assembly of claim 16, wherein subsidiary paraffin discharge holes to discharge the paraffin solution to the outside are formed at inner corners of the load part adjacent to the at least one fixing rib.

18. The embedding assembly of claim 16, wherein the at least one rib fixing groove of the embedding cassette is an integrated fib fixing groove formed at one side of the edge of the embedding cassette and the at least one fixing rib of the embedding mold is an integrated fixing rib formed at one side of the edge of the embedding mold.

19. The embedding assembly of claim 16, wherein the embedding mold further includes insertion grooves, configured to partially accommodate the side surfaces of the embedding cassette, and outer walls.

20. The embedding assembly of claim 16, wherein guide protrusions to guide insertion of the embedding cassette are formed at one side of the at least one fixing rib; and guide grooves are formed in the at least one rib fixing groove of the embedding cassette.

\* \* \* \* \*